United States Patent [19]

Cook, Jr.

[11] 3,946,073
[45] Mar. 23, 1976

[54] PROCESS FOR PREPARATION OF UREA AUTOCONDENSATION PRODUCT

[75] Inventor: William H. Cook, Jr., Lake Jackson, Tex.

[73] Assignee: The Dow Chemical Company, Midland, Mich.

[22] Filed: Dec. 9, 1974

[21] Appl. No.: 530,337

Related U.S. Application Data

[63] Continuation-in-part of Ser. No. 427,594, Dec. 26, 1973, abandoned, which is a continuation of Ser. No. 865,209, Oct. 9, 1969, abandoned.

[52] U.S. Cl............................................ 260/553 B
[51] Int. Cl.$^2$...................................... C07C 127/24
[58] Field of Search .............................. 260/553 B

[56] References Cited

UNITED STATES PATENTS 2,918,467  12/1959  Hibbitts et al.................. 260/553 B

OTHER PUBLICATIONS

Mutzenburg et al., Chem. Eng., 1965, pp. 175–190.

Primary Examiner—Arthur P. Demers
Attorney, Agent, or Firm—Gary D. Street; Walter J. Lee

[57] ABSTRACT

Urea is pyrolyzed in a falling film reactor at a temperature of from about 180° to about 240°C. A short residence time in the reactor provides for good urea conversion with minimal formation of other autocondensation pyrolyzates.

4 Claims, No Drawings

3,946,073

PROCESS FOR PREPARATION OF UREA AUTOCONDENSATION PRODUCT

CROSS-REFERENCE TO RELATED APPLICATIONS

This application is a continuation-in-part of my copending application Ser. No. 427,594, filed Dec. 26, 1973 now abandoned which is a streamlined continuation of application Ser. No. 865,209, filed Oct. 9, 1969, now abandoned.

BACKGROUND OF THE INVENTION

The present invention relates to the preparation of biuret and more particularly is concerned with a pyrolysis process employing a falling film reactor for preparing biuret with good urea conversion.

The preparation of biuret by pyrolysis of urea, as well as other methods, has long been known in the art. Many of these preparations are summarized in an article "Biuret and Related Compounds" published in Chemical Reviews, 56 p. 95–197 (1956). Of the various methods for preparing biuret set forth in this review article it was indicated that although difficulties are present, large scale preparations have been developed based on the pyrolysis of urea.

Olin (U.S. Pat. No. 2,370,065) teaches a process for preparing biuret wherein urea is heated to a temperature above its melting point but below the decomposition temperature of the biuret and by-product ammonia formed by the condensation of urea is swept from the reaction zone with a stream of a hydrocarbon gas. In the practice of the Olin process, the hydrocarbon gas, preferably toluene, is introduced during the reaction period below the surface of the molten urea and the ammonia-hydrocarbon gas mixture rapidly removed from the reaction zone. The ammonia is removed from the resulting hydrocarbon sweep gas-ammonia mixture and the ammonia depleted hydrocarbon gas returned to the reaction zone for removal of further quantities of ammonia.

Harmon (U.S. Pat. No. 2,145,392) teaches a process for preparing biuret by heating urea at a temperature of 130° to 205°C. at a pressure of not substantially greater than 200 mm. of mercury. This allegedly provides a mixture of urea and biuret from which the biuret is subsequently separated.

Kamlet (U.S. Pat. No. 2,768,895) lists a number of references directed to the preparation of biuret by pyrolysis of urea and teaches a process for directly pyrolyzing urea in the absence of a catalyst at a temperature between 120° and 205°C. This effects substantial autocondensation of the urea to produce a mixture of unreacted urea and an admixture of urea autocondensation products, the total mixture consisting of 30 to 70 percent urea with biuret being a predominant component of the autocondensation products. The Kamlet process further includes extracting urea from the resulting product with a selective solvent for urea, e.g. preferably water, to leave a product containing 60 to 90 percent of the admixed autocondensation products with the remainder being urea. The so-extracted product mass is taught to be suitable for use as a protein supplement for ruminant feeds.

Formaini et al (U.S. Pat. No. 3,057,918) teaches a cyclic process for preparing biuret in which urea is heated at from 135° to 200°C. and the resulting crude pyrolytic product quenched and digested in hot aqueous ammonia until no triuret remains. The liquid mass is then cooled to fractionally crystallize biuret which is removed. The ammonia is stripped from the residual solution whereupon cyanuric acid crystallizes. This solid product is separated from the residual aqueous solution and the solution concentrated by removal of water. The resulting concentrate is recycled with additional urea for subsequent pyrolysis.

Colby (U.S. Pat. No. 2,861,886), Kamlet, (referenced hereinbefore) and other publications attest to the utility of biuret as a feed composition additive for ruminants. This additive provides usable nitrogen to supplement the protein content of feeds from natural sources.

Each of the hereinbefore listed processes for pyrolyzing urea into biuret in general consists of reacting urea in a molten reaction mass over prolonged periods of time to achieve appreciable conversion to the desired biuret product. Correspondingly, the co-production of other urea condensation products, e.g. triuret, ammelide and cyanuric acid in detrimental amounts many times results. Formation of such undesired by-products is favored at the higher temperatures, which at the same time are preferred for maximum production of biuret.

It is a principal object of the present invention to provide a urea pyrolysis process for production of biuret in good yields and with a short reaction time.

It is another object of the present invention to provide a process for production of biuret which assures for good control of reaction conditions and provides for ready recovery of any urea based reactant which might be lost from the system during the processing.

It is also an object of the present invention to provide a high temperature-short reaction time process for preparing biuret by pyrolysis of urea wherein autocondensation by-product formation, particularly cyanuric acid, is held to a low level.

It is another object of the present invention to provide a process for preparing a biuret product by pyrolysis of a urea feedstock wherein there is direct rapid conversion of urea.

These and other objects and advantages of the process of the present invention readily will become apparent from the detailed description presented directly hereinafter.

GENERAL SUMMARY

In general, the present process comprises introducing a urea feedstock into a falling film reactor at a controlled flow rate, passing the urea based material as a thin film through the reactor at a flow rate such that the biuret pyrolysis product temperature is maintained at from about 180° to about 240°C. as the product exits from the reactor, removing evolved ammonia from the reaction system as it is formed, and recovering the biuret product.

DESCRIPTION OF PREFERRED EMBODIMENTS

In the practice of the present invention, preferably a molten urea feedstock or feed material hereinafter at times referred to simply as urea at an initial temperature of from about 130° to about 150°C.; usually as from about 135° to 145°C. is introduced into a falling film reactor, which provides a product exit temperature of from about 180° to about 240°C. and preferably from about 195° to about 230°C. The flow rate (i.e. equivalent residence time) of the urea feed material ranges from about 180 pounds of actual urea compound/hour/foot of reactor cylinder periphery (lb./hr./ft.) to about 600 lb./hr./ft.; for highest conversion of urea to biuret with minimal formation of cyanuric acid and other autocondensation pyrolyzates, a flow rate of from about 430 to about 520 lb./hr./ft. is employed. The optimum temperature to be employed at the preferred flow rate to produce a product having a consistently high biuret content and a low cyanuric acid level ranges from about 215° to about 225°C. At this higher temperature the amount of cyanuric acid by-product is increased.

At flow rates lower than that set forth, conversion to biuret is not appreciably enhanced but formation of other autocondensation pyrolyzate products is markedly increased. If the flow rate is increased to provide higher mass velocities the conversion to biuret decreases. This apparently results from poor filming tendencies at the high flows coupled with the fact that the system becomes loaded heatwise so that the temperature cannot reach the preferred level.

By-product ammonia evolved during the conversion can be removed either countercurrently or cocurrently with the downward flow of the reaction mass. Because of the thin film of reactants, this gaseous by-product readily escapes from the melt without need for sparging or flushing; this is an additional advantage of the present process. Advantageously, a slight reduction in pressure, i.e. a partial vacuum can be maintained on the system to aid in removal of the ammonia by-product gas. Alternatively, a very light flow of an inert gas, e.g. a nitrogen, argon, low-boiling hydrocarbon, such as, for example, the saturated aliphatic compounds having from 1 to about 10 carbon atoms (i.e. methane, ethane, straight and branched chain propanes, butanes, pentanes, hexanes, heptanes, octanes, nonanes and decanes) and the like, can be passed through the reactor system to maintain a flow of the ammonia off-gas to a scrubber-absorber or other ammonia recovery apparatus.

The recovered biuret product resulting from the short term residence in the falling film reactor usually contains from about 20 to about 40 percent or more by weight of biuret. The biuret product can be used as prepared. Additionally, this material can be employed directly as a feedstock for further pyrolysis in any of a variety of processes to effect further conversion of the urea contained therein to biuret, or in certain instances, if desired, other autocondensation products. Alternatively, the urea can be removed by extraction with a polar liquid which is a solvent for urea but in which the biuret product is insoluble or only poorly soluble. This provides both for removal and recovery of urea for reuse, if desired, as well as further upgrades the product with respect to its biuret content. Water is a particularly effective solvent; methanol, ethanol, and the like polar liquids which are solvents for urea also can be employed.

In addition to urea itself other urea feedstocks which have been found to be suitable for use in the present process are mixtures of urea and biuret (and other urea condensation products) having a biuret concentration up to about 25 percent or more. Such a reactant might be obtained, e.g. from passage through a falling film reactor at a reaction temperature lower than indicated hereinbefore or by pyrolyzing a melt of urea. Additionally, an aqueous solution of urea can be employed. The concentration of urea in such aqueous feedstocks is not critical. It is only necessary that the feed rate and rate of water vaporization be balanced to assure that the urea component is present in a quantity that assures formation of the reactant film in the reactor.

As is known by those skilled in the art, a falling film reactor is an apparatus which spreads a thin film of liquid reaction medium on one side of an impervious surface, heat being supplied to or removed from the other side of the surface. The precise structure of the reactor is not critical, a number of diverse structures being known. Those which are commercially available generally comprise a metal cylinder or plurality of metal tubes or cylinders surrounded by a heat-exchange jacket, and are designed to disperse the liquid reaction medium along the internal surface of the cylinder, heat exchange being effected through the surface of the cylinder or cylinders. In general, the thickness of the reacting film is in the range of 0.03 to 0.10 inch. Devices to regulate film thickness are sometimes employed; however, in many such devices, the cylinder is positioned with its axis in a vertical direction and film thickness is uneven, and limited by fall of the film due to gravity.

Of particular interest in the practice of the present invention are those thin film reactors described as "agitated". In these reactors, usually positioned with the cylinder axis in a horizontal direction, a mechanical member located within the cylinder and revolving therewithin serves to keep the film at its desired thickness and also usually to propel the liquid through the cylinder. A detailed discussion of such agitated thin film reactors is found in Volume 72, Number 19 of Chemical Engineering (Sept. 13, 1965), pages 175–190, inclusive.

It is apparent from the foregoing that the present process offers a number of advantages over the conventional mass pyrolysis techniques set forth hereinbefore as representative of the prior art. These include: There is no need for maintaining large amounts of purge gas for ammonia removal an the corresponding large volume scrubbing equipment to recover the ammonia from the dilute reactor off-gas stream. The engineering of large scale commercial operations is simplified. Parameters employed for calculating variables of reaction temperature and reactant flow rates for a falling film reactor are considerably less complicated than the parameters which must be considered in agitation calculations, i.e. for mass reactors. Because of the short residence time in the reactor, the process can be run at temperatures much higher than conventionally employed. This provides for more rapid conversion to biuret without a corresponding increase in the rate of formation of other autocondensation products. Since the formation of these other pyrolyzate co-products is dependent on the biuret and urea concentrations, the true plug-flow, i.e. a steady streamline or laminar flow, precludes backmixing of the biuret product with fresh feed of urea and thus reduces the chance for formation of other pyrolyzates. In large scale operations shut-down procedures are simplified since there is no massive product or reactant hold-up in the system.

The following Examples will serve to further illustrate the present invention but are not meant to limit it thereto.

EXAMPLE 1

A jacketed, stainless steel falling film reactor having an internal diameter of 1½ inches and a length of 20 feet was heated to a predetermined temperature by Dowtherm heat exchange fluid. Molten urea at a temperature of from about 135°–140°C. was fed into the top of the reactor, flowing as a film through notches; i.e. grooves, in the inside wall of the pipe, the resulting pyrolysis condensation product being collected from a sealed leg overflow at the bottom of the reactor. The entire system is maintained under a slightly reduced pressure (approximately 5 inches of water or about 750 mm Hg absolute) thereby providing an updraft of evolved vapors. The effluent gas is passed through a scrubber where it is contacted directly in counterflow relation with fresh molten urea feed thereby removing any urea entrapped in the effluent vapors and returning this to the falling film reactor. This not only minimizes urea losses but also serves to clean up the ammonia by-product.

A number of runs were made wherein the mass velocity (lb. urea feed/hr./ft.) and reaction temperature were varied. The reaction temperature was determined by measuring the temperature of the condensation product as it exited from the falling film reactor.

The results of these studies are summarized in Table I.

Table I

| Run No. | Feed Mass Velocity (lb./hr./ft.) | Feed Rate (lb./hr.) | Product Effluent Temp. (C°) | PRODUCT Biuret (wt.%) | Cyanuric Acid (wt.%) |
| --- | --- | --- | --- | --- | --- |
| 1 | 186 | 73 | 200 | 27.1 | 0.6 |
| 2 | 184 | 72 | 213 | 36.3 | 2.5 |
| 3 | 186 | 73 | 220 | 39.8 | 3.5 |
| 4 | 186 | 73 | 226 | 38.7 | 5.2 |
| 5 | 186 | 73 | 234 | 40.1 | 10.2 |
| 6 | 241 | 94.5 | 215 | 35.6 | 2.7 |
| 7 | 239 | 93.5 | 221 | 39.0 | 3.3 |
| 8 | 241 | 94.5 | 228 | 40.2 | 8.5 |
| 9 | 263 | 103 | 195 | 14.3 | 0.6 |
| 10 | 262 | 102 | 215 | 32.8 | 1.0 |
| 11 | 262 | 102 | 220 | 38.9 | 2.5 |
| 12 | 264 | 104 | 229 | 44.3 | 5.5 |
| 13 | 297 | 116 | 195 | 27.4 | 1.3 |
| 14 | 390 | 152.5 | 223 | 34.0 | 4.22 |
| 15 | 395 | 155 | 216 | 32.8 | 1.9 |
| 16 | 430 | 170 | 224 | 42.3 | 1.55 |
| 17 | 443 | 175 | 220 | 40.2 | 2.68 |
| 18 | 511 | 202 | 224 | 40.45 | 1.42 |
| 19 | 511 | 202 | 227 | 41.7 | 2.39 |
| 20 | 585 | 231 | 221 | 37.5 | 0.78 |
| 21 | 600 | 237 | 219 | 38.2 | 4.72 |
| 22 | 610 | 239 | 214 | 34.0 | 1.43 |
| 23 | 653 | 258 | 213 | 29.5 | 0.92 |

The balance of the pyrolyzate was found primarily to be unconverted urea.

EXAMPLE 2

Using the same reactor system as described in Example 1, aqueous urea solutions containing about 90–95 weight percent urea were employed as the feedstock. In separate runs, a given solution was introduced into the top of the reactor, the biuret product being recovered as described in Example 1.

The results of this study are summarized in Table II.

Table II

| Run No. | Feed Mass Velocity (lb/hr/ft)* | Feed Rate (lb/hr)* | Prod. Effluent Temp. (C°) | Product Composition Biuret (wt. percent) | Cyanuric Acid (wt. percent) | $H_2O$ (wt. percent) |
| --- | --- | --- | --- | --- | --- | --- |
| 1 | 230–269 | 91–106 | 219–220 | 34.0 | 2.33 | 9.6 |
| 2 | 245–267 | 100–105 | 209–210 | 30.3 | 0.86 | 9.7 |
| 3 | 380 | 150 | 221 | 37.1 | 4.1 | 4.8 |
| 4 | 380 | 150 | 224 | 38.8 | 5.4 | 4.8 |
| 5 | 392 | 155 | 226 | 34.3 | 4.18 | 6.5 |
| 6 | 443 | 175 | 220 | 34.0 | 2.73 | 6.4 |

*expressed as actual weight of urea in solution.
No noticeable hydrolysis was found in using the aqueous urea feedstock.

I claim:
1. A process for preparing biuret which comprises
   a. introducing a urea feedstock, said feedstock being urea or a mixture of urea, biuret and other urea autocondensation products, into a heated falling film reactor,
   b. passing said urea feedstock through said heated reactor as a thin film and at a flow rate of from about 180 to about 600 pounds of actual urea feedstock/hour/foot of reactor cylinder periphery (lb/hr/ft) which provides a biuret pyrolysis product exiting from said reactor at a temperature of from about 180°C. to about 240°C.,
   c. removing evolved ammonia from the falling film reactor system as it is formed, and
   d. recovering the biuret product.

2. The process as defined in claim 1 wherein the urea feedstock is molten urea at an initial temperature of from about 130° to about 150° C.

3. The process as defined in claim 2 wherein the biuret product temperature is maintained at from about 195° to about 230°C. as said product exits from said reactor.

4. The process as defined in claim 2 wherein the molten urea feedstock as introduced into the falling film reactor is at a temperature of from about 135° to about 145°C., said urea passes through said reactor at a flow rate of from about 430 to about 520 lb./hr./ft. and the biuret product temperature is maintained at from about 215° to about 225°C., as said product exits from said reactor.

* * * * *